United States Patent [19]

Mitchell

[11] Patent Number: Plant 7,141

[45] Date of Patent: Feb. 6, 1990

[54] VARIETY OF TROPICAL MANGO NAMED ED MITCHELL

[76] Inventor: Edward F. Mitchell, 13950 SW. 67 Ave., Miami, Fla. 33158

[21] Appl. No.: 155,477

[22] Filed: Feb. 12, 1988

[51] Int. Cl.[4] ..... A01H 5/00

[52] U.S. Cl. ..... Plt./33

[58] Field of Search ..... Plt./33

*Primary Examiner*—Robert E. Bagwill

*Attorney, Agent, or Firm*—Malin, Haley, McHale, DiMaggio & Crosby

[57] ABSTRACT

A new variety of tropical mango originating from a sucker that sprouted from a root of a Keitt Mango tree. The new variety is characterized by a fruit averaging 18 to 19 oz. and having a bright green underside with blended shades of yellow and peach on most of the surface. The fruit flesh is bright yellow with a small seed.

2 Drawing Sheets

BRIEF SUMMARY OF THE INVENTION

A new variety of tropical mango which resulted from a sucker that sprouted from the root of a Keitt Mango tree that had been frozen down in a freeze. The tropical mango is characterized by having an upright vigorous growing tree with long and well distributed branches. The tree flushes in late summer and early fall and blooms in January and February of each year. The fruit is generally similar in shape to a Keitt Mango, but the average size is smaller. The fruit of the new variety of tropical mango averages 18 to 19 oz. The fruit is characterized by a bright green on the underside with blending shades of yellow and peach on most of the surface of the fruit. The flesh of the fruit is bright yellow and only has a small amount of fiber. The flavor of the fruit is excellent. The seed size is small in comparison to fruit size. The fruit can be held on the tree very late and can be picked after most of the Keitt Mango trees have been picked. The fruit seems to be resistant to Anthracnose.

BRIEF DESCRIPTION OF THE DRAWINGS

FIG. 1 is a photograph of a portion of the tree bearing fruit.

FIG. 2 is a close-up photograph with a ruler showing the size and color of the fruit and illustrating the flesh of a sliced piece of fruit.

FIG. 3 is a close-up photograph of the fruit and leaves.

DETAILED DESCRIPTION OF THE PREFERRED EMBODIMENT

A new variety of tropical mango is shown in the drawings FIGS. 1 through 6. The mango of the instant disclosure is referred to as the Mitchell mango. This variety of Tropical Mango resulted from a sucker that sprouted from the root of a Keitt Mango tree. The Keitt Mango tree had been frozen down by a prior freeze.

The tree characteristics are illustrated in FIG. 1 through FIG. 3. The tree is characterized by having an upright vigorous growing tree with long and well distributed branches as shown. The tree flushes in late summer and early fall of each year. The tree blooms in January and February of each year.

The characteristics of the fruit are shown in detail in FIGS. 2 and 3. The fruit is somewhat similar in shape to a Keitt Mango. But the fruit's average size is smaller than the Keitt Mango. The fruit averages 18 to 19 oz. in weight. The diameter of the fruit is approximately $4\frac{3}{4}$ inches to 5 inches in length and $3\frac{3}{4}$ inches to 4 inches in width.

The fruit's external coloring is distinct. The color characteristics include a bright green ground color with blending shades of yellow and peach on most of the surface of the fruit overlying the ground color. The fruit exhibits colors near 144B, 13D and 46D, with the green portion tending to disappear as the fruit matures. The flesh of the fruit is bright yellow near 15B, with only a small amount of fiber. The flavor is excellent. The seed size is small in comparison to fruit size, on the order of 1 inch in width, or about one-third the width of the fruit, and on the order of $1\frac{1}{3}$ inches in length, or about one-third the length of the fruit, as shown by the position of the cut of the mango in FIG. 2 being approximately $\frac{1}{3}$ of the way away from the outside edge of the fruit toward the center of the fruit.

The fruit can be held on the tree very late and be picked after most of the Keitts have been picked. The fruit seems to be resistant to Anthracnose. All the characteristics of this fruit make it very desirable as a commercial variety. Several other trees have been propagated from the original tree.

The characteristics of the leaves are shown in FIG. 3. The leaves are long and narrow with distinct veins. Specifically, the leaves average between 6 inches and 12 inches in length and between 1 inch and 3 inches in width.

The instant invention has been shown and described herein in what is considered to be the most practical and preferred embodiment. It is recognized, however, that departures may be made therefrom within the scope of the invention and that obvious modifications will occur to a person skilled in the art.

The color values expressed herein are those of the R.H.S. Colour Chart.

What I claim is:

1. A new and distinct variety of tropical mango substantially as described and illustrated having a fruit characterized by a bright green underside with blended shades of yellow and peach on most of the surface of the fruit.

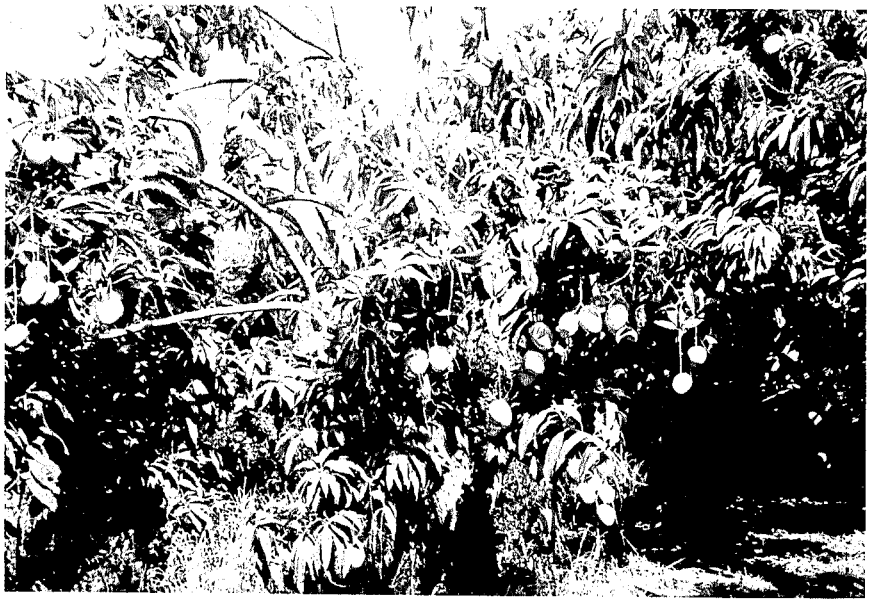
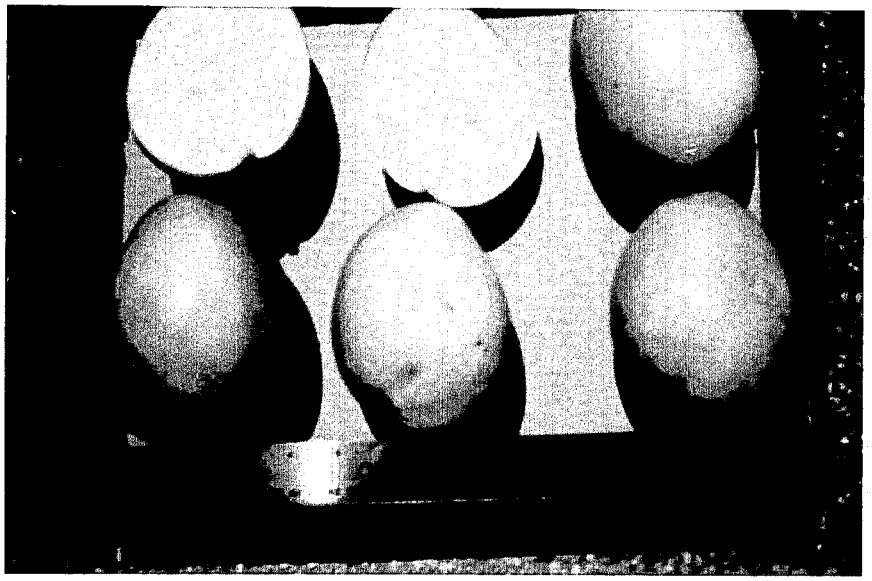

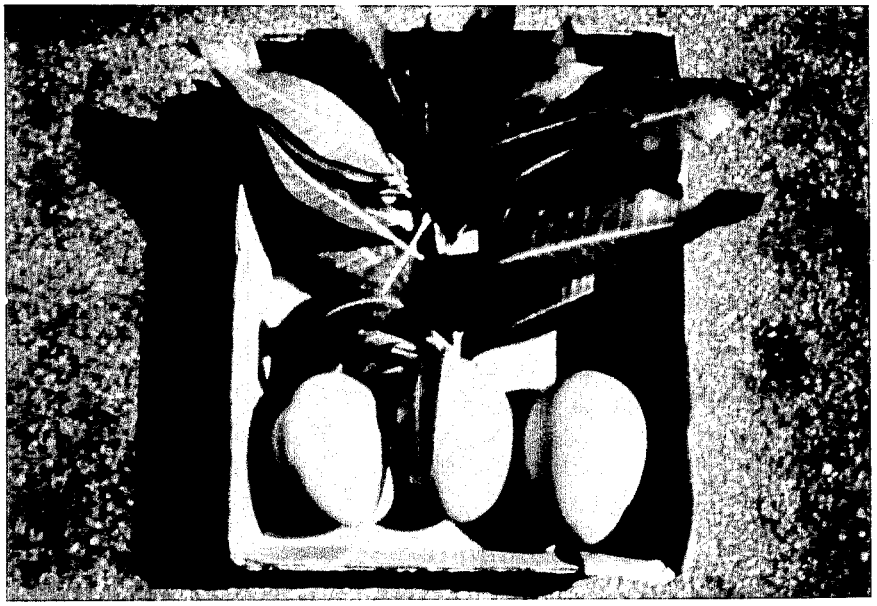

* * * * *